United States Patent [19]

Ufermann

[11] Patent Number: 4,787,890
[45] Date of Patent: Nov. 29, 1988

[54] FEEDING SYSTEM FOR ENTERAL FEEDING

[75] Inventor: Rüdiger Ufermann, Moers, Fed. Rep. of Germany

[73] Assignee: Fresenius AG, Bad Homburg von der Hohe, Fed. Rep. of Germany

[21] Appl. No.: 1,723

[22] Filed: Jan. 9, 1987

[30] Foreign Application Priority Data

Jan. 10, 1986 [DE] Fed. Rep. of Germany ....... 8600458
Apr. 3, 1986 [DE] Fed. Rep. of Germany ....... 3611112

[51] Int. Cl.$^4$ .............................................. A61M 1/00
[52] U.S. Cl. .................... 604/128; 604/129; 604/250; 604/251; 604/260; 604/411; 222/204; 248/95; 340/613
[58] Field of Search ............... 604/244-246, 604/251-262, 80, 81, 128, 322, 129, 411-414; 128/DIG. 3; 248/95-100; 340/613; 222/166, 204

[56] References Cited

U.S. PATENT DOCUMENTS

| | | |
|---|---|---|
| 682,269 | 9/1901 | Poe ...................................... 604/128 |
| 778,311 | 12/1904 | Grisell ................................. 604/128 |
| 2,131,516 | 9/1938 | Leffert et al. ....................... 604/128 |
| 3,163,176 | 12/1964 | Darling ........................ 128/DIG. 13 |
| 3,670,728 | 6/1972 | Dabney ............................... 604/251 |
| 3,934,474 | 1/1976 | Whitinger .......................... 604/246 |
| 4,137,915 | 2/1979 | Kamen ................................ 604/246 |
| 4,161,179 | 7/1970 | Abramson . | |
| 4,432,763 | 2/1984 | Manscgit et al. . | |
| 4,496,354 | 1/1985 | Steer et al. ......................... 604/322 |
| 4,509,861 | 4/1985 | Sjönell ................................ 604/183 |
| 4,655,763 | 4/1987 | Malcolm et al. ................... 604/411 |

FOREIGN PATENT DOCUMENTS

| | | |
|---|---|---|
| 0119373 | 3/1983 | European Pat. Off. . |
| 0117202 | 4/1930 | Fed. Rep. of Germany ...... 604/261 |
| 1282046 | 5/1962 | France . |
| 2377806 | 1/1977 | France . |
| 1397101 | 6/1975 | United Kingdom ................ 604/128 |

OTHER PUBLICATIONS

Fresensius Diatetic, Frenta System, Dated 2/8/83.

Primary Examiner—C. Fred Rosenbaum
Assistant Examiner—Mario Costantino
Attorney, Agent, or Firm—Townsend and Townsend

[57] ABSTRACT

The invention relates to a feeding system (1) for enteral feeding comprising a container (2) preferably constructed as a disposable article for receiving the food. Said container (2) is disposed in a suspension means (3) which is constructed such that the container (2) in the suspended state points with its opening (5) upwardly and assumes a position inclined to the horizontal. As a result when the tubing system (4) is introduced into the container for supplying the nutrient solution to the patient no leaks can occur because the opening (5) points upwardly so that along the periphery of a piercing tube (17) introduced into the container (12) no solution can drip out. Nevertheless, due to the inclined position of the container (2) and the arrangement of the end of the inserted piercing tube (17) at the lowermost point (6) of the container (2) all the solution can be extracted; for this purpose for the extraction preferably a drip chamber (21) is provided in connection with a tube clamp (26).

24 Claims, 5 Drawing Sheets

FEEDING SYSTEM FOR ENTERAL FEEDING

BACKGROUND OF THE INVENTION

The invention relates to a feeding system for enteral feeding according to the preamble of claim 1.

Hitherto known feeding systems for enteral feeding have a container for accommodating the nutrient substance or food, said container having an opening which is provided with a pierceable closure or which is rupturable. The container is suspended by means of a suspension means and connected to a flexible tubing system whose one end is disposed in the container whilst the other end is led to the person to be fed.

The disadvantage here is however that as container either glass bottles or jars are used into which the food preparation must first be filled. Thereafter the containers are suspended with the opening pointing downwards this disposition nearly always leads to leaks so that part of the nutrient solution drips out of the container and does not reach the tubing system. As investigations carried out within the framework of the invention have shown this situation could not be remedied even by attempting to pierce the container laterally because in this case as well the undesirable leaks also occurred.

SUMMARY OF THE INVENTION

It is therefore the object of the invention to provide a feeding system for enteral feeding which uses a container for receiving food which container has a pierceable or rupturable closure in which leaks in the container accommodating the food or nutrient solution can be reliably avoided.

According to the invention, a disposable liquid feeding container is disposed in a suspension means with an opening having a rupturable closure which is directed inwardly of the container and oriented in a preselected angular position inclined to the horizontal and a piercing tube is provided which is inserted into the container so that the opening of the tube is located in the lowermost point within the container.

As a result leakage problems cannot occur at all because the container is suspended so that its opening points upwardly and thus nutrient solution cannot come out of the opening in the region surrounding the end disposed in the container. To ensure that in spite of this arrangement of the container the entire nutrient solution can be withdrawn therefrom, the container is suspended inclined at an angle to the horizontal and the end of the tubing system disposed in the container, which is formed as a piercing tube and arranged with its open end at the lowermost point of the container. If for example the container is one having a rectangular form the suspension results in insertion of the piercing tube approximately along one of the diagonals of the container into the latter and the opening of the piercing tube or insert tube thus comes to lie in the region of one of the corners so that in this manner and, by vacuum extraction of the nutrient solution, withdrawal is possible even when the opening is pointing upwardly.

By using a container constructed as a disposable article the further advantage is obtained that transferring the nutrient solution to other separate containers for the feeding system is not necessary. This saves work and material costs. The disposable containers in which the nutrient solution is sold can be used directly although their opening as a rule is sealed only with a simple cellophane or aluminium layer which would not produce any sealing effect whatever with the piercing tube inserted. As stated however this is not necessary with the arrangement according to the invention because the container is in any case arranged with the opening pointing upwards.

In particularly simple manner the inclined suspension of the container can be achieved by a suspension means constructed according to a specific embodiment in which a holding means is provided into which the container is inserted and on which a suspension member can be secured formed for example as a plate or strip. This suspension member can be secured formed for example as a plate or strip. This suspension member is arranged at an angle to the holding means so that the container in the suspended state under the force of gravity automatically moves into the desired tilted position without further steps being necessary for this purpose. The magnitude of the angle depends above all on the container form and size. For possible adaptation to different container types when using one suspension means it would be conceivable to secure the suspension member movably on the holder frame so that a setting of the particular angle desired is possible.

The arrangement of the suspension member on the holding means may for example be such that the longitudinal axis of the suspension member extends at an angle to the longitudinal axis of the holding means, in particular the suspension member and the holding means include an angle $\alpha$ of $140° \pm 10°$. The arrangement can furthermore be such that the longitudinal axis of the receiving member and the transverse axis of the holding means extend at an angle to each other which is not equal to 90°, in particular the longitudinal axis of the receiving member and the transverse axis of the holding means include an angle $\beta$ of $70° \pm 10°$. It is likewise within the scope of the invention to arrange the two members such that they are arranged both at the said angle $\alpha$ and at the said angle $\beta$.

An embodiment for the holding means which is particularly simple to make is a holder frame of three plates which can be adapted to the particular form of the container to be received so that a receiving space for the container is formed. As materials for example plastics or light metals can be used, and the securing of the container in the receiving space can be further increased by providing at least two holding tabs arranged in pairs which are each disposed on one plate and engage round the container at the sides which are not held by the plates.

If the container, with respect to the tilted position thereof, comprises in the region of its upper edge a tab pointed away from said container it suffices for the holding means to be formed as a plate having a slot adapted to the dimensions of the tab for receiving the latter. Conveniently, the plate comprises a portion directed away from the suspension member and a second portion adjoining the first portion and facing towards the suspension member, the slit being disposed in the region of the joint between the two portions. The container with the slit is reliably held by the two portions arranged substantially parallel to each other. Preferably, the free end of the second portion comprises a recess adapted to the dimensioning of the tab of the container. As a result containers with tabs of smaller dimensions can be reliably fixed by the plate by the tab bearing laterally on the outer boundary of the recess.

The securing of the container can be additionally increased by holding tabs or tongues disposed laterally of the plate. During emptying of the container the latter is pivoted slightly about the suspension point of the suspension member due to the changing combined centre of gravity of container and suspension means.

In an advantageous embodiment of the invention in the suspension means a pointer is pivotally mounted with which on the basis of the changing angular position of the suspension means the container weight can be determined. The pointer is prefereably made hook-shaped in the region of its end facing the suspension point and the end passes through the hole for suspension on the suspension means having in particular a notch directed towards the holding means. About the base point of the notch the pointer can adapt itself to the pivot motion of the suspension means and the container when the latter is emptied and thus indirectly indicate the container weight. The notch-shaped hole also has the advantage that when the pointer for indicating the container weight is omitted a tube end can be clamped in the notch. Alternatively, the container weight can be determined by the suspension means being provided with a spring-loaded member and a scale.

To facilitate extraction of the nutrient solution from the container a pumpable drip chamber can be disposed in the tubing system by means of which the nutrient solution can be extracted from the container, whereafter the solution from the drip chamber can be supplied directly or possibly via an interposed hose pump to the patient.

A particularly preferred embodiment of the drip chamber is one of resiliently compressible material with which firstly air can be pumped into the container, whereafter the liquid extraction by suction takes place when the drip chamber expands again.

To further facilitate the extracation the drip chamber can be followed by a tube clip in the tubing system which shuts off the tube end coming from the drip chamber during the extraction operation.

BRIEF DESCRIPTION OF THE DRAWINGS

Further details, features and advantages of the invention will be apparent from the following description of several examples of embodiment with the aid of the drawings, wherein.

DESCRIPTION OF SPECIFIC EMBODIMENTS

Figures 1, 2:
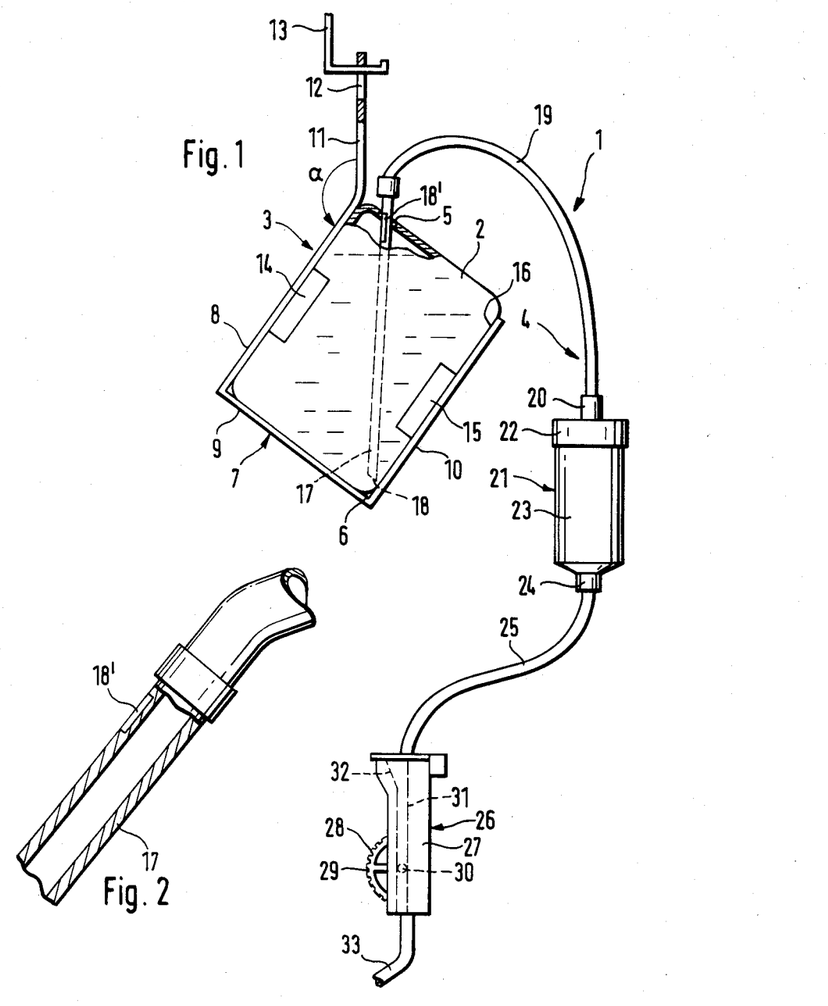
FIG. 1 shows a schematically slightly simplified view of a feeding system according to the invention comprising a first embodiment of a suspension means.
FIG. 2 shows an illustration corresponding to FIG. 1 representing a longitudinal section through a piercing tube of the system according to the invention.
Figure 3:
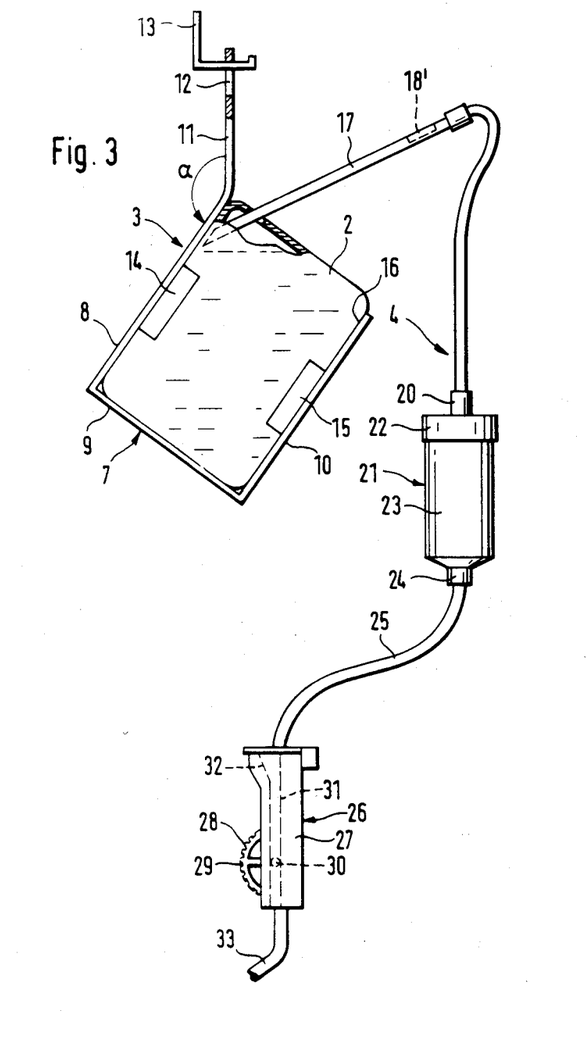
FIG. 3 shows a representation corresponding to FIG. 1 of the feeding system during the piercing of a container of the system according to the invention.

FIGS. 1-3 illustrate a feeding system 1 which comprises a container 2 preferably constructed as dispensable article for receiving the food, preferably liquid food, a suspension means 3 for suspending the container and a tubing system 4 for supplying the food to a patient not shown in the drawings.

As is apparent from FIGS. 1 and 3 the container 2 is arranged in the suspension means 3 in such a manner that in the suspended state it assumes an angle to the horizontal so that in the case of the example a corner 6 of the container 2 forms the lowermost point. For this purpose the suspension means 3 is constructed so that the container 2 in the suspended state assumes the position illustrated in said figures solely under the action of gravity. The suspension means comprises for this a holder frame 7 which in the embodiment illustrated comprises three plates 8,9, and 10 each arranged substantially at a right-angle to each other. The plates 8, 9 and 10 may either be integrally formed with each other or joined together in some other manner, for example by welding or adhesion. A suspension member 11 is secured to the holder frame 7. The longitudinal axis 50 of the suspension member 11 includes with the longitudinal axis 51 of the plate 8 an angle $\alpha$ which in the embodiment illustrated is chosen so that the rectangular or parallelepiped container 2 assumes the position illustrated in said figures in which the opening 5 points upwardly and one of the corners, in the case illustrated the corner 6, forms the lowermost point of the container 2. As a rule the angle will be about 150°±10°. The transverse axis of the plate 8 not illustrated in the drawings extends at a right-angle to the longitudinal axis 50 of the suspension member 11.

In the example of the embodiment of FIGS. 1 to 3 the suspension member 11 is integrally joined to the holder frame 7, but it may also be articulately connected to the holder frame 7 via a self-locking hinge so that setting of the angle $\alpha$ is possible depending on the desired inclination of the container 2. The suspension member 11, which may be formed as strip or plate, comprises a cutout or recess 12 into which a portion of a stationary securing means can be introduced as indicated in FIGS. 1 and 3 by a hook 13.

As further apparent from these figures in the case of the example on each plate 8 and 10 two holding tabs are disposed of which only the front holding tabs 14 and 15 can be seen. These serve to reliably secure the container 2 in a receiving space 16 defined by the plates 8, 9 and 10.

The tubing system 4 comprises in the feeding system 1 according to the invention a piercing tube 17 which forms the end of the tubing system 4 disposed in the container 2 and comprises a piercing tip 18 and a vent notch 18' which is arranged at the periphery and in the upper region of the piercing tube 17 and extends parallel to the longitudinal direction thereof, this arrangement and construction being apparent in detail from FIG. 2. The piercing tube 17 is introduced through the closure member of the opening 5 into the container 2 and disposed at the lowermost point thereof, such as the corner 6 in the case of the example, so that the entire nutrient solution contained in the container 2 can be withdrawn in spite of the upwardly directed opening 5.

The piercing tube 17, which can also be formed as independent part, is adapted to be fitted onto a conduit 19 disposed outside the container 2 and in flow communication via a connection 20 with a drip chamber 21. The drip chamber 21 comprises a cover 22, a cylindrical main body 23 consisting in the case of the example of resiliently compressible material and a further connection member 24. Connected to said member 24 is s further conduit 25 which opens into a tube clamp 26. Said tube clamp 26 comprises a guide member 27 for a clamp wheel 28 which has a ribbed surface 29. The clamp wheel 28 is provided with a stud which is not shown in detail and which extends beyond the side regions of the clamp wheel 28 and comprises two ends extending beyond the side region of the clamp wheel 28, one end 30 of which is indicated in the Figure in plan view. Said end 30, like the opposite end, slides in a guide recess which extends over the entire length of the tube clamp and which has a widened region 32. If the cross-section of the conduit or tube 25 is to be released the clamp wheel 28 is led in the direction towards the widened region 32 and as a result it moves away from the conduit 25 and thus releases the cross-section. In the opposite direction the clamp wheel 28 clamps the tube walls together and in this manner completely blocks the tube cross-section. This position is indicated in the Figure.

Following the tube clamp 26, that is in the conduit 33 leading away from the tube clamp 26 and to the patient, it is possible to dispose a hose pump which is not illustrated in the Figure.

Now, to supply a patient with nutrient solution firstly the container 2 is disposed in the suspension means 3, after which the latter is suspended on the hook 13 and as a result due to the action of gravity the position of the container shown in FIG. 1 arises with upwardly directed opening 5 and an inclination to the horizontal. Thereafter the piercing tube 17 is inserted through the pierceable closure of the opening 5 initially in a first phase of the piercing operation according to FIG. 3 up to about one third into the container 2. In this condition illustrated in detail in FIG. 3 the piercing tube 17 is close to the piercing opening 5 so that no solution can emerge.

In this condition the pumping operation by means of the drip chamber 21 is started during which the proportioning or tube clamp 26 is closed. At the start the piercing tube 17 is therefore only introduced up to about one third into the container 2 since the latter is completely filled with solution without any air content and consequently on complete introductin of the piercing tube 17, when the vent notch 18' would be disposed in the opening 5, solution or food could run out of the container.

After this first phase in a second phase illustrated in FIG. 1 the piercing tube is introduced into the container 2, in the example illustrated along the diagonal thereof, until the opening to the piercing tube 17 has reached the lowermost point 6 of the container. In this position of the piercing tube the vent notch 18' is disposed in the opening 5 so that said notch 18' can perform its function, i.e. vent the container 2, without solution being to run out of the container 2. In this condition the tube clamp 26 is opened.

Thereafter the nutrient solution can be further withdrawn from the container and for this purpose in the case of the example the drip chamber 21 disposed between the tube clamp 26 and the container 2, being also arranged beneath the lowermost point of the container 2, is compressed, made possible because of the resiliently compressible material. When this is done firstly any air which might still be disposed in the conduit 19 is introduced into the container 2 because previously the tube clamp 27 was shut off. When the drip chamber expands again after the compression solution is sucked out of the container 2 into the drip chamber 21 so that a continuous liquid column arises from the lowermost point of the container 2 up to the drip chamber and consequently after the initial extraction by compression of the drip chamber 21 solution is now continuously withdrawn from the container 2. This solution is supplied to the patient after passing through the drip chamber 21 via the opened tube clamp 26 either under the action of gravity or by an addittionally interposed pump.

As FIG. 1 shows, in this arrangement any leakage of the container 2 by undesirable dripping of the solution through the opening 5 and along the outer periphery of the piercing tube 17 is effectively prevented because even without the provision of special sealing means no such dripping out can occur because the opening 5 points upwardly. Nevertheless, because of the inclined arrangement of the container 2 complete emptying thereof is ensured.

FIGS. 4–10 show further embodiments of the suspension means 3 for suspending the container 2. Parts corresponding in their effect to the suspension means 3 according to the illustration of FIGS. 1–3 have been denoted by the same reference numerals.

To avoid repetitions the complete feeding system has not been illustrated.

The above remarks on the feeding system apply accordingly to the embodiments outlined below.

The suspension means according to FIGS. 4–10 serve to receive the container 2 which is made as disposable article of rectangular form but in the region of its two upper opposite edges comprises triangular tabs of tongues 55 and 56. The securing of the container 2 to the suspension means 3 is in a manner to be described in detail in the region of the tab 55.

Figures 4, 5:
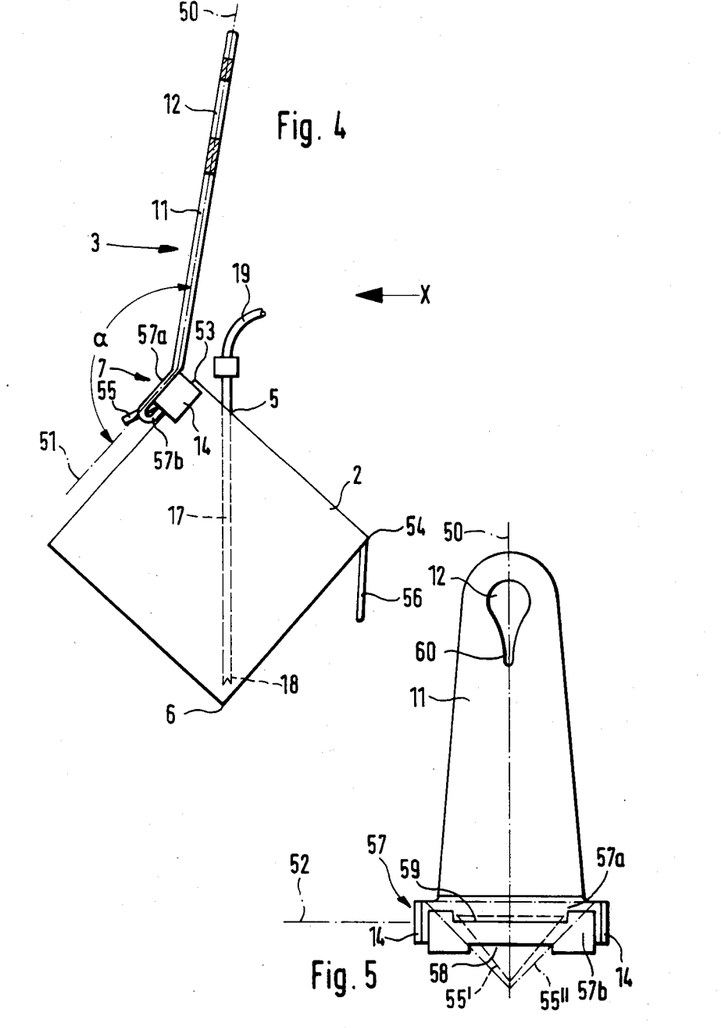
FIG. 4 shows a second embodiment of a suspension means for the system according to the invention.
FIG. 5 shows the suspension means in the view x according to FIG. 4.

In the emdodiment of FIGS. 4 and 5 the holding means 7 is constructed as plate 57 to which the suspension member 11 is secured. The longitudinal axis 50 of the suspension member 11 includes with the longitudinal axis 51 the angle $\alpha$ already discussed with regard to the previous embodiment. The plate 57 consists of a first portion 57a directed away from the suspension member 11 and a second portion 57b adjoining the first portion 57a and directed towards the suspension member 11, and in the region of the connection of the two portions 57a, 57b a slot 58 extending transversely of the portions is disposed. Securing of the container 2 to the suspension member 11 is effected in that the container 2 with its tab 55 is introduced from above between the two portions 57a and 57b of the plate 57, the pointed end of the tab 55 passing through the slit 58. The two portions 57a and 57b are spaced so that the tab 55 can just be pushed between them and is clamped between the portions 57a and 57b by the weight of the container 2. In FIG. 5 positions are shown which a small tab 55' or a large tab 55" would assume in the inserted state. To ensure that the container 2 is reliably held by the holding means 7 holding tabs 14 are disposed either side of the plate 57. The free end of the portion 57b comprises a cutout 59 which is adapted to the dimension of the smaller tab 55' so that said tab 55' is securely held between the two lateral boundaries of the cutout 59.

As apparent from the illustration of FIG. 5 the longitudinal axis 50 of the receiving member 11 extends at a right-angle to the transverse axis 52 of the plate 57. The cutout 12 in the suspension member 11 has a notch which is directed towards the plate 57 and into which the conduit 19 can be clamped after removal of the piercing tube 17 from the container 2. In contrast to the embodiment of the piercing tube 17 according to FIGS. 1 and 3, as apparent from FIG. 4 the piercing tube 17 is notched at its lower and 18, thereby effectively preventing any clogging of the piercing tube 17.

Figures 6, 7, 8:
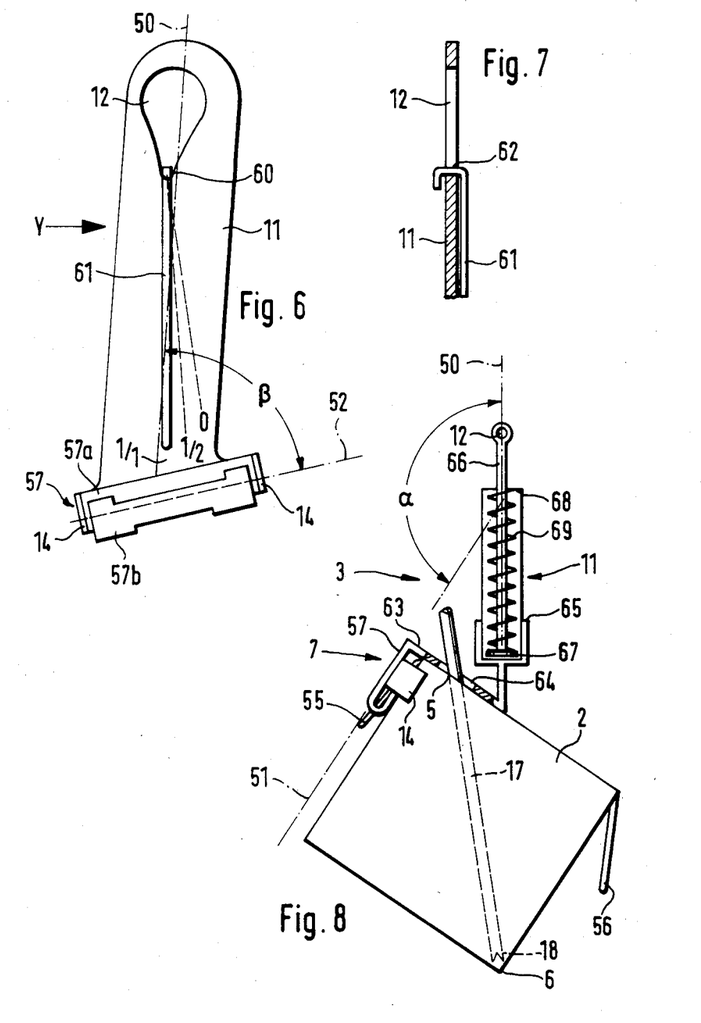
FIG. 6 shows a third embodiment of a suspension means for the system according to the invention.
FIG. 7 shows the suspension region of the suspension means in the direction y of FIG. 6.
FIG. 8 shows a fourth embodiment of a suspension means for the system according to the invention.

The emdodiment of FIGS. 6 and 7 corresponds substantially to the embodiment of FIGS. 4 and 5. As a difference therefrom, as apparent from FIG. 6 the longitudinal axis 50 of the receiving member 11 is at an angle β to the transverse axis 52 of the plate 57 which is not equal to a right-angle and is in particular 70°±10°. The angle α corresponds to the angle α of the embodiment of FIGS. 4 and 5 although it is also possible to provide an angle α of 180°.

As further apparent from FIG. 6 the recess or cutout 12 is disposed eccentrically, i.e. it is located on the side of the suspension member which includes an obtuse angle with the transverse axis 52. The cutout 12 also has a notch 60 and a pointer 26 is suspended therein. The container weight can be determined by means of the pointer 26 because the suspension member 11 due to the changing centre of gravity of the container 2 and suspension member 11 during emptying of the container executes a pivot movement about the suspension point thereof. Markings in the region of the lower end of the pointer indicate the quantity still remaining in the container. FIG. 6 shows which position the pointer 61 assumes with respect to the suspension member 11 when the container is 1/1, ½ full or empty. It is obvious that the intermediate positions illustrated n dashed line indicate only the position of the pointer with respect to the suspension member 11 whilst in reality the supension member 11 of course pivots about the suspension point thereof. Experiments have shown that the container weight can be determined by this simple pointer arrangement with an accuracy of about 10%. The pointer arrangement is particularly simple when the pointer 61 is provided in the region of the cutout 12 with a hook 62 which can be simply hung in the notch 60.

In the embodiment of FIG. 8 the holding means 7 comprises adjoining the plate 57 a cover plate 63 extending perpendicularly thereto. Secured to the free end of the cover plate 63 is the suspension member 11 and the longitudinal axis 50 thereof again includes with the longitudinal axis 51 of the plate 57 an angle α of about 140°±10°. The angle β is not shown in FIG. 8 but as in the embodiment of FIG. 4 or 5 may be 90° or 70°±10° as in the embodiment of FIGS. 6 and 7. Provided in the cover plate 63 is a cutout 64 for insertion of the piercing tube 12. The suspension member 11 comprises a cylinder 65 in which a piston 67 provided with a piston rod 66 is guided and between the cylinder cover 68 and the piston 67 there is a pressure spring 69. The end of the piston rod remote from the piston 67 is provided with a cutout 12. The formation of the suspension member 12 in the manner of a spring-loaded component provides a further possibility of optically displaying the emptying of the container 2. Thus, for example, on the piston rod 66 a marking can be disposed which provides direct information on the remaining weight in the container 2. It is also conceivable for the movement of the plunger or piston 67 to be transmitted to a control element which is not illustrated and which on a specific plunger travel blocks the tube system so that no more food is supplied to the patient.

Figures 9, 10, 11:
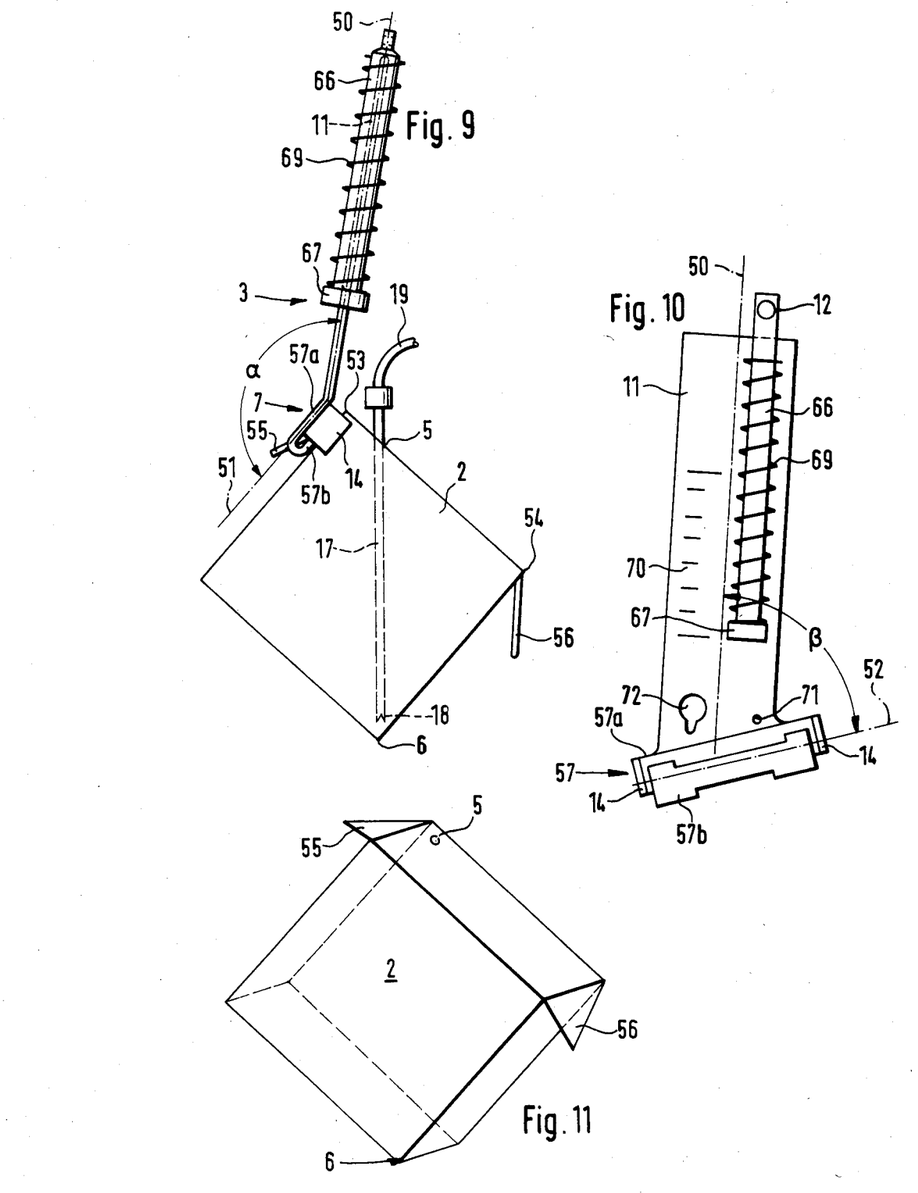
FIG. 9 shows a fifth embodiment of a suspension means for the system according to the invention.
FIG. 10 shows the suspension region of the suspension means in the direction Z of FIG. 9
FIG. 11 shows a container for use with the feeding system according to the invention.

The embodient according to FIGS. 9 and 10 corresponds substantially to the embodiment of FIG. 6. In contrast to the latter, as apparent from FIG. 9 instead of the pointer 61 a spring-loaded member similar to that in FIG. 1 is disposed on the receiving member 11. Said spring-loaded member consists of a piston rod 66, a piston 67 and a pressure spring 69. The piston 67 is movable in the receiving member 11 and guides the pressure spring 69 which bears at the other end on the receiving member 11. The spring-loaded receiving means is fixedly secured with the cutout 12.

It is apparent from FIG. 10 that the spring-loaded member 66; 67; 69 is disposed eccentrically on the receiving member 11, ensuring that the angle α of about 140° is maintained. Immediately adjacent the spring-loaded member 66, 67, 69 which is formed as spring balance a scale 70 is disposed on which with the aid of a marking not shown on the piston 67 the container weight or container contents amount can be read on corresponding displacement of the piston 67 by emptying of the container 2.

The receiving member 11 further comprises a marking 71 which clearly indicates that the opening 5 of the container 2 must be located in the immediate vicinity of said marking 71. This excludes any improper positioning of the container 2.

A notch-shaped passage 72 is provided on the receiving member 11 to clamp the tube 19 in slip-free manner after emergence of the piercing tube 17 from the container 2 or serve as suspension element.

FIG. 11 shows in a perspective view the container 2 used in the feeding system according to the invention. Said container is preferably constructed as disposable article when required in rectangular form and comprises an opening 5 which is sealed for example by a foil and into which the piercing tube 17 is introduced. The closure tabs 55 and 56 are clearly apparent. The container 2 is adapted to be inserted into the plate 57 or holder frame 7 so that the opening 5 is brought into the immediate vicinity of the marking 7 and the closure tab 55 is inserted into the slot 58 provided. After the fixed securing of the suspension means 3 the container 2 has its lowest point at the corner 6. Such containers 2 generally consist of waxed paperboard and have in their interior a liquid-impermeable layer of a plastic or aluminium foil. The are usually used for packaging milk, fruit juices, liquid food and the like.

The invention has now been explained with reference to specific embodiments. Other embodiments will be apparent to those of ordinary skill in the art. It is therefore not intended that the invention be limited except as indicated by the appended claims.

I claim:

1. A feeding system for enteral feeding comprising:
    a container for receiving the food, the container having an opening which is provided with a pierceable or rupturable closure;
    a suspension means for the container; and
    a tubing system having a first end and a second end, said first end being disposed in the container and said second end for coupling to a person to be fed, said suspension means suspending the container with said opening (5) directed upwardly and inclined at an angle to the horizontal; and wherein said first end comprises a piercing tube (17) with an end opening (18), said piercing tube (17) protruding through said container opening (5), said end opening being disposed at the lowermost point (6) of the container (2) upon suspension by said suspension means.

2. The feeding system according to claim 1, wherein the suspension means (3) comprises a holding means (7) for the container (2) and a suspension member (11) which is secured to said container and which is disposed at an angle (α, b) to the holding means (7) such that the container (2) in a suspended state assumes a tilted position.

3. The feeding system according to claim 2, wherein a first longitudinal axis (50) of the suspension member (11) extends at an angle to the a second longitudinal axis (51) of the holding means (7), said first longitudinal axis and said second longitudinal axis are disposed to include an angle of 140 degrees plus or minus 10 degrees.

4. The feeding system according to claim 2, wherein a first longitudinal axis (50) of the suspension member (11) and a transverse axis (52) of the holding means (7) extend at an angle different than 90° to each other, and the first longitudinal axis (50) of the suspension member (11) and the transverse axis (52) of the holding means (7) include an angle β of 70°±10°.

5. The feeding system according to claim 2, wherein the holding means is constructed as a holder frame which comprises three plates (8,9,10) which define a receiving space (16) conforming to the form of the container (2) to be received.

6. The feeding system according to claim 5, wherein on at least two of the plates (8,9,10) first and second holding tabs (14,15) are disposed.

7. The feeding system according to claim 2, wherein the piercing tube (17) has a vent notch (18').

8. The feeding system according to claim 1, wherein the container (2) comprises in the region of its upper edge (53) a third tab (55) directed away from the container (2) and the holding means (7) is constructed as a plate (57) having a slit (58) adapted to the dimension of the third tab (55) for receiving the third tab.

9. The feeding system according to claim 8, wherein the plate (57) comprises a first portion (57a) directed away from the suspension member (11) and a second portion (57b) adjoining the first portion (57a) and directed towards the suspension member (11), the slit (58) being disposed in the region of a joint between the first portion and the second portion (57a, 57b).

10. The feeding system according to claim 9, wherein a free end of the second portion (57b) comprises a cutout (59) adapted to the dimension of the third tab (55) of the container (2).

11. The feeding system according to claim 8, wherein holding tabs (14) are disposed laterally of the plate (57).

12. The feeding system according to claim 1, wherein the suspension means (11) comprises a spring-loaded member (65,66,67,68,69) for determining the container weight.

13. The feeding system according to claim 12, wherein a pointer (61) is pivotally mounted on the suspension means so that the container weight can be determined based on the changing angular position of the suspension means (11).

14. The feeding system according to claim 13, wherein the suspension means (11) with the spring-loaded member (66,67,69) comprises a scale (70) for determining the container weight.

15. The feeding system according to claim 1, wherein the suspension means (11) has a marking (71) for defining the position of the opening (5) of the container (2).

16. The feeding system according to claim 1, wherein the suspension means (11) comprises a cutout (12) for suspending the suspension means (11) having a notch (66) directed towards the holding means (7).

17. The feeding system according to claim 1, wherein the suspension point of the suspension means (11) is disposed eccentrically with respect to the longitudinal axis (50) of the suspension member (11).

18. The feeding system according to claim 1, wherein a pumpable drip chamber (21) is disposed following the piercing tube (17) in the tube system (4).

19. The feeding system according to claim 18, wherein the drip chamber (21) comprises of resiliently compressible material.

20. The feeding system according to claim 18, wherein a tube clamp is disposed following the drip chamber (21) in the tube system (4).

21. The feeding system according to claim 1, wherein the tube system (4) includes means for connecting to a hose pump.

22. The feeding system according to claim 1 where said first end opening (18) of the piercing tube (17) comprises a notch.

23. The feeding system to claim 1, wherein the piercing tube (17) is formed as independent part and adapted to be fitted onto the end of the tube (19).

24. The feeding system according to claim 1, wherein the suspension means comprises a notch-shaped passage (72) for clamping one end of the tube (19).

* * * * *